United States Patent [19]

Harris

[11] Patent Number: 4,536,349

[45] Date of Patent: Aug. 20, 1985

[54] FURAN DERIVATIVES USEFUL AS AROMA COMPOUNDS

[75] Inventor: Eugene G. Harris, West Chester, Ohio

[73] Assignee: National Distillers and Chemical Corporation, New York, N.Y.

[21] Appl. No.: 426,527

[22] Filed: Sep. 29, 1982

[51] Int. Cl.$^3$ .......................... A61K 7/46; C11B 9/00
[52] U.S. Cl. ................................................ 252/522 R
[58] Field of Search .................................... 252/522 R

[56] References Cited

U.S. PATENT DOCUMENTS

| | | | |
|---|---|---|---|
| 3,227,731 | 1/1966 | Kulka | 252/522 R X |
| 3,252,998 | 5/1966 | Ohloff et al. | 252/522 R X |
| 3,668,134 | 6/1972 | Lamberti et al. | 252/522 R X |
| 3,764,567 | 10/1973 | Wakayama et al. | 252/522 R |
| 3,917,870 | 11/1975 | Slangan et al. | 252/522 R |
| 3,940,502 | 2/1976 | Winter et al. | 549/472 X |
| 4,013,593 | 3/1977 | Shaffer et al. | 252/522 R |
| 4,261,904 | 4/1981 | Takeda et al. | 252/522 R X |
| 4,404,127 | 9/1983 | Van Der Weertt et al. | 252/522 R |

OTHER PUBLICATIONS

Chemical Abstracts, 85 177470j (1976).
Chemical Abstracts 83 42783b (1975).
Chemical Abstracts 68 59397s (1968).
Chemical Abstracts 97 215971f (1982).
Barbot et al., J. Organometallic Chem. 170(1) 1–8, (1979).

*Primary Examiner*—Helen M. S. Sneed
*Attorney, Agent, or Firm*—Kenneth D. Tremain; Gerald A. Baracka

[57] ABSTRACT

Furan derivatives, useful as fragrances, having the formula

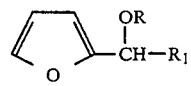

wherein R is alkyl or alkenyl and $R_1$ is alkyl, alkenyl, cycloalkyl, cycloalkenyl or aryl.

2 Claims, No Drawings

FURAN DERIVATIVES USEFUL AS AROMA COMPOUNDS

BACKGROUND OF THE INVENTION

This invention relates to certain furan derivatives and more particularly to ether derivatives of furyl-substituted alcohols, useful as fragrances.

Furan derivatives are known as perfume and flavor enhancers. For example, U.S. Pat. No. 3,764,567 discloses 2-(1'-hydroxymethyl-ethyl)-5-methyl-5-vinyl-tetrahydrofuran as having a lilac flower fragrance. U.S. Pat. No. 3,940,502 discloses certain furfuryl-alkyl or arylethers as flavor enhancers. U.S. Pat. No. 3,227,731 discloses 1-(α-furyl)-2,2-dialkyl-1,3-dihydroxypropane carbonates useful in perfume compounding. Moreover, *Organic Chemistry,* 1946, 7185–7186, discloses the preparation of certain methyl and ethyl ether derivatives of lower alkyl ($C_1$–$C_4$) 2-furylcarbinols. None of these, however, are disclosed or suggested as fragrances or fragrance components.

The growing demand in recent years for perfumes with a pronounced green note has spurred interest in new synthetics that are chemically stable, are diffusive, and have a natural odor character. Most of the materials that are currently available are aldehydic in nature and thus suffer from instability in basic media.

SUMMARY OF THE INVENTION

Accordingly, it is one object of the present invention to provide novel furan derivatives.

Another object of this invention is to provide furan derivatives, particularly suitable as perfume ingredients.

Still another object of the present invention is to provide novel furan derivatives which have natural green odors useful in many types of fragrance formulations.

These and other objects are accomplished herein by providing furan derivatives having the general formula:

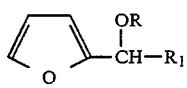
(I)

wherein R is an alkyl group having from 1 to about 6 carbon atoms or an alkenyl group having from about 3 to about 6 carbon atoms and $R_1$ is selected from the group consisting of alkyl, alkenyl, cycloalkyl, cycloalkenyl and aryl and perfume compositions containing the same.

DETAILED DESCRIPTION OF THE INVENTION

The furan derivative aroma compounds of the present invention can be prepared according to the following synthetic scheme:

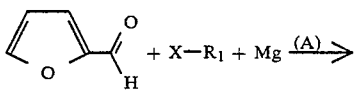

-continued

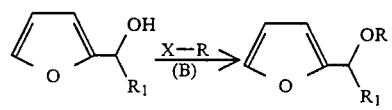

wherein X is halogen, such as chloro, bromo or iodo and R and $R_1$ are as defined hereinabove.

As is readily apparent from the above reaction scheme, furyl-substituted alcohols are initially prepared by the reaction of furfural with a Grignard reagent. To obtain the Grignard reagent, a halo-alkane, such as bromoalkane, in an equal volume of anhydrous diethylether or other solvent, such as tetrahydrofuran is typically added to magnesium metal, at either reflux or other suitable temperatures, as low as $-10°$ C., depending on the nature of the halogen compound. Generally, a 1:1 to 1:2 mole ratio of halo compound to magnesium is used, preferably 1:1 to 1:1.3, respectively. Addition times range from about 40 minutes to about 4 hours, with the best yields resulting when the addition time is approximately one hour. After stirring for one hour, furfural is added over a period of, for example, one hour, to the Grignard reagent. The mole ratio of furfural:Grignard reagent is generally about 1:1 to 1:2 and preferably 1:1 to 1:1.3. The mixture becomes very thick. When the furfural addition is completed, the mixture is stirred for about one hour.

Generally, to isolate the 1-furylalcohol intermediate, two workup procedures may be utilized. For example, when $R_1$ is saturated or if the intermediate alcohol is stable to acid, the crude mixture is poured onto ice containing concentrated hydrochloric acid. The layers are separated and the water layer is extracted, for example, three times with ether; the organic layers are combined and dried over magnesium sulfate. Filtration and removal of solvent gives the desired intermediate alcohol.

The second workup procedure can be used, when $R_1$ is unsaturated or if the alcohol is acid sensitive. A saturated ammonium chloride solution is added slowly to the crude reaction mixture. After stirring about 1–2 hours, the mixture is filtered and then the layers are separated. The water layer is extracted with a solvent, such as hexane three times, for example. The organic layers are combined and dried over magnesium sulfate. Filtration and removal of solvent gives the desired intermediate alcohol.

Short-path distillation is sufficient to give good intermediate alcohol products, except for alcohols, such as 1-furyl-1-phenyl methanol and 1-furyl ethanol which are sensitive to polymer formation. Alcohols of this nature need to be distilled in a manner which avoids polymer formation, such as, for example, distilled in the presence of a polymerization inhibitor, e.g. several weight % sodium carbonate.

The preparation of the final products of the present invention (step B in the above illustrated reaction scheme) is carried out by reacting the furyl alcohol with an alkylating agent in a basic medium and in the presence of a phase transfer reagent. This is typically accomplished by charging the intermediate furyl alchol and a phase-transfer reagent to a reaction flask, equipped with a mechanical stirrer. Adequate agitation is important for this reaction.

Phase transfer reagents contemplated for use herein include quaternary ammonium compounds such as:

trimethylbenzylammonium chloride;
triethylbenzylammonium chloride;
hexadecyltrihexylammonium bromide;
trioctylethylammonium bromide;
tridecylmethylammonium chloride;
didodecylmethylammonium chloride;
dimethyldodecyl-α-methylbenzylammonium chloride;
tetramethylammonium chloride;
tetrabutylammonium chloride;
tetrabutylammonium iodide;
tetrabutylammonium bisulfate;
tetraheptylammonium iodide;
tetranonylammonium hydroxide;
dioctadecyldimethylammonium chloride;
α-methylbenzyldimethylbenzylammonium chloride;
bornylbenzyldimethylammonium chloride;
tridecylbenzylammonium chloride;
α-methylbenzylmethylbenzyldodecylammonium chloride;
tricosylmethylammonium chloride;
tricaprylylmethylammonium chloride;
tricaprylyldodecylammonium p-toluene sulfonate;
cetyltrimethylammonium bromide;
cetyldimethylethylammonium bromide;
stearyldimethylbenzylammonium chloride;
stearylamidoethyltrimethylammonium chloride;
stearylamidoethyltrimethylammonium ethasulfate; and
myristyltrimethylammonium bromide.

Whereas the amount of phase transfer reagent can vary from about 0.5 to 25 mole percent of the 1-furylalcohol, most generally about 1 to 10 mole percent phase transfer reagent is employed, based on the alcohol. The phase transfer reagent may vary depending on the product being prepared. For example, for the preparation of methyl ethers, tetrabutylammonium iodide is generally used in amounts, for example, of about 2 mole percent of the alcohol. For the preparation of other ethers, such as ethyl ethers, tetrabutylammonium bisulfate has been found to be an especially advantageous phase transfer reagent.

Prior to the addition of the alkylating agent to the alcohol, a 50% aqueous caustic solution, such as sodium hydroxide, for example, (5:1 mole ratio of sodium hydroxide:alcohol) is added to the alcohol over a period of from about 15 to 30 minutes. The alkylating agent (X-R) is then added for example, in mole ratios of X-R:alcohol of 1:1 to 5:1 and preferably 1:1 to 3:1 over 10-45 minutes. The rate of addition depends on the ease and rate of stirring. The alkylating agent for making methyl ethers, is, for example, dimethylsulfate. Ethyl and pentyl ethers are generally prepared by using bromoethane and bromopentane, respectively. Other alkylating agents include 2-bromopropane, n-pentyl ester of p-toluene-sulfonic acid, 1-bromo-2-methylpropane and the like. The mixture is stirred for about 2-5 hours. Isolation of the products generally consists of pouring the reaction mixture into distilled water, separating the layers, and washing the organic layer, e.g., three times, with water. The product is taken up in ether and dried over magnesium sulfate.

While certain of the compounds within formula I hereinabove are known compounds (not as fragrances, however), other compounds within the scope of the present invention and particularly with the following formula II are novel:

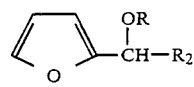

wherein R is as defined hereinabove and $R_2$ is selected from the group consisting of alkyl, alkenyl, cycloalkyl, cycloalkenyl and phenyl, with the proviso that when $R_2$ is alkyl having from 1 to 3 carbon atoms, the R group contains more than 2 carbon atoms. Illustratively, compounds which are prepared in accordance with the above procedure and which are within the scope of Formulas I and II above include 2-(1-methoxy-3-pentenyl)furan, 2-(1-ethoxy-4-methylpentyl)furan, 2-(1-ethoxyhexyl)furan, 2-(methoxy, phenylmethyl)furan, 2-(1-methoxy-4-methylpentyl)furan, 2-(1-methoxyhexyl)furan and 2-(1-pentoxyethyl)furan.

As a class, the compounds of the present invention are characterized by their unique, powerful, and penetrating odors having a general green theme. Depending on the structures of R, $R_1$ and $R_2$, these compounds have green odors ranging from fruity green, to vegetable green, to a fresh leaf green. Surprisingly, the compounds are characterized by a fullness of body most notably found in materials of natural, rather than synthetic, origin.

As a result of their pleasing and long lasting aroma, the furan derivatives of the present invention are useful as fragrances in the preparation and formulation of fragrance compositions, such as perfumes and perfumed products. Perfume compositions and the use thereof in cosmetics, detergent and bar soap formulations and the like are exemplary of the utility thereof.

The compounds of this invention can be used in concentrations of from trace amounts up to about 20 percent of the fragrance formulation into which they are incorporated. As will be expected, the concentration of the compound will vary depending on the particular furan derivative employed, the particular fragrance desired in the composition, etc.

The following examples are presented by way of illustration and not by way of limitation so that those skilled in the art may better understand how to practice the present invention.

EXAMPLE 1

17.3 grams (0.61 moles) of magnesium is combined with a small amount of diethyl ether sufficient to cover the metal in a 1-liter flask fitted with mechanical stirrer, condenser, addition funnel and nitrogen inlet and methyl iodide (94.5 g; 0.67 mole) in an equivalent volume of ether added at a rate sufficient to maintain reflux. When the reaction to form the Grignard reagent is complete, 64.3 g (0.67 mole) furfural is added at room temperature over 1½ hour period. The reaction mixture is then worked up by the addition of 200 mls saturated aqueous ammonium chloride solution, filtration to remove the solids, and separation of the aqueous and organic layers. The water layer is extracted with ether and the combined ether portions dried over magnesium sulfate. Crude 1-furylethanol is recovered by evaporation of the ether solvent and short-path distilled over 2 weight percent sodium carbonate to obtain 1-furylethanol (B.p. 44°-66° C. at 0.5 mm Hg; approximately 90% pure as determined by gas chromatographic analysis).

Ten grams of the distilled 1-furylethanol (0.089 mole) is charged to a reactor with 0.61 g (2 mole percent) tetrabutylammonium bisulfate and 19.2 g of a 50 percent aqueous solution of sodium hydroxide added over a 15 minute period with stirring. This is followed by addition of 34.7 g (0.25 mole) 1-bromopentane over a period of 15 minutes and the reaction mixture allowed to stir for 3 hours. The reaction mixture is then extracted with diethyl ether which, after drying over magnesium sulfate, is evaporated. The resulting crude product is short-path distilled to obtain 2-(1-pentoxyethyl)furan in low yield (B.p. 35° C. at 0.2 mm Hg.). The structure of the 2-(1-pentoxyethyl)furan

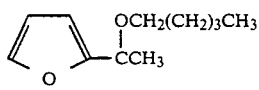

is confirmed by infrared and nuclear magnetic resonance spectroscopy.

nmr(CDCl$_3$) 7.5(1H,M); 6.4(2H,M); 4.5(1H,M); 3.45(2H,T); 1.5(6H,M); 1.0(6H,M)δ odor: The product has a fresh, green odor reminiscent of crushed leaf.

EXAMPLE 2

15.1 grams (0.62 mole) of magnesium is combined with a small amount of diethyl ether sufficient to cover the metal in a 1-liter flask fitted with mechanical stirrer, condenser, addition funnel and nitrogen inlet and methyl iodide (97.3 g; 0.62 mole) in an equivalent volume of ether added at a rate sufficient to maintain reflux. When the reaction to form the Grignard reagent is complete, 54.7 g (0.57 mole) furfural is added at room temperature over 1 hour and stirred for an additional 2 hour period. The reaction mixture is then worked up by the addition of 450 mls saturated aqueous ammonium chloride solution, filtration to remove the solids, and separation of the aqueous and organic layers. The water layer is extracted with ether and the combined ether portions dried over magnesium sulfate. Crude 1-furylethanol is recovered by evaporation of the ether solvent and short-path distilled over 2 weight percent sodium carbonate to obtain 1-furyl-1-phenyl-methanol (B.p. 100° C. at 0.5 mm Hg; approximately 90% pure as determined by gas chromatographic analysis).

9 grams of the distilled 1-furyl-1-phenyl-methanol (0.052 mole) is charged to a reactor with 0.39 g (2 mole percent) tetrabutylammonium iodide and 10.4 g of a 50 percent aqueous solution of sodium hydroxide added over a 10 minute period with stirring. This is followed by addition of 17.6 g (0.14 mole) 1-bromopentane over a period of 10 minutes and the reaction mixture allowed to stir for 2 hours. The reaction mixture is then extracted with diethyl ether which, after drying over magnesium sulfate, is evaporated. The resulting crude product is short-path distilled to obtain 2-(methoxy, phenylmethyl)furan in low yield.

The structure of the 2-(methoxy, phenylmethyl) furan

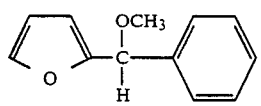

is confirmed by infrared and nuclear magnetic resonance spectroscopy.

nmr(CDCl$_3$) 7.36(6H,M); 6.25(2H,M); 5.27(1H,S); 3.35(3H,S)

odor: The product has an intense fruity green odor.

EXAMPLE 3

30.7 grams (1.28 moles) of magnesium is combined with a small amount of anhydrous THF sufficient to cover the metal in a 1-liter flask fitted with mechanical stirrer, condenser, addition funnel and nitrogen inlet and crotyl bromide (80% technical grade; 100 g) in an equivalent volume of THF added at a rate sufficient to maintain reflux. When the reaction to form the Grignard reagent is complete, 36.5 g (0.38 mole) furfural in 40 ml THF is added at room temperature over 1 hour and stirred for an additional 1½ hour period. The reaction mixture is then worked up by the addition of 200 mls saturated aqueous ammonium chloride solution, filtration to remove the solids, and separation of the aqueous and organic layers. The water layer is extracted with THF and the combined THF portions dried over magnesium sulfate. Crude 1-furyl-3-pentenyl-alcohol is recovered by evaporation of the THF solvent and short-path distilled over 2 weight percent sodium carbonate to obtain 1-furylethanol (B.p. 56° C. at 1.8 mm Hg; approximately 90% pure as determined by gas chromatographic analysis).

Ten grams of the distilled 1-furyl-3-pentenylalcohol (0.07 mole) is charged to a reactor with 0.51 g (2 mole percent) tetrabutylammonium iodide and 14.4 g of a 50 percent aqueous solution of sodium hydroxide added over a 15 minute period with stirring. This is followed by addition of 22.7 g (0.18 mole) dimethylsulfate over a period of 10 minutes and the reaction mixture allowed to stir for 2 hours. The reaction mixture is then extracted with diethyl ether which, after drying over magnesium sulfate, is evaporated. The resulting crude product is short-path distilled to obtain in low yield (B.p. 37°–41° C. at 1.0 mm Hg). The structure of the 2-(1-methoxy-3-pentenyl) furan

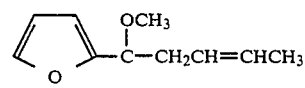

is confirmed by infrared and nuclear magnetic resonance spectroscopy.

nmr(CDCl$_3$) 7.4(1H,M); 6.3(2H,M); 4.0(1H,T); 2.57(2H,M); 4.85–5.8(2H,M); 3.25(3H,S); 1.0(3H,D)

odor: The product has an intense sweet green odor.

EXAMPLES 4–7

The following compounds, within the structure

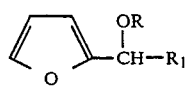

are prepared following the same or similar procedure as described in Examples 1 to 3.

| Examples | $R_1$-Group | R-Group | % Yield (distilled) | Odor | nmr(CDCl$_3$) |
|---|---|---|---|---|---|
| 4 | —CH$_2$CH$_2$CH$_2$CH$_2$CH$_3$ | —CH$_3$ | 64.5 | Fresh, leafy green odor with aspects reminiscent of jasmine | 7.35(1H,M); 6,28(2H,M); 4.1(1H,T); 3.15(3H,S); 1.75(2H,M); 1.2(6H,M); 0.75(3H,T) |
| 5 | —CH$_2$CH$_2$CH(CH$_3$)$_2$ | —CH$_3$ | 69.5 | Green, leafy/vegetable odor with nuances reminiscent of aspects of jasmine and marigold. | 7.4(1H,M); 6.35(2H,M); 4.1(1H,T); 3.4(3H,S); 1.5(5H,M); 0.75 and 0.85(6H,D) |
| 6 | —CH$_2$CH$_2$CH$_2$CH$_2$CH$_3$ | —CH$_2$CH$_3$ | 58.7 | Fruity green/vegetable green odor | 7.34(1H,M); 6.3(2H,M); 4.2(1H,T); 3.4(2H,M); 1.5-2.1(6H,M); 1.0-1.4(5H,M); 0.8(3H,D)δ |
| 7 | —CH$_2$CH$_2$CH(CH$_3$)$_2$ | —CH$_2$CH$_3$ | 55.6 | Fresh green odor with subtle nuances reminiscent of rose and marigold | 7.5(1H,M); 6.4(2H,M); 4.3(1H,T); 3.5(2H,M); 1.5-2.1(5H,M); 0.75-1.4(6H,D)δ |

Obviously, other modifications and variations of the present invention are possible in the light of the above teachings. It is therefore to be understood that changes may be made in the particular embodiments of this invention which are within the full intended scope of this invention as defined by the appended claims.

What is claimed is:

1. A process for providing a composition with a fragrance comprising incorporating therein an odoriferous amount of a compound having the structure:

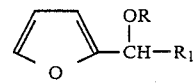

wherein R is an alkyl group having from 1 to about 6 carbon atoms or an alkenyl group having from about 3 to about 6 carbon atoms and $R_1$ is selected from the group consisting of alkyl, alkenyl, cycloalkyl, cycloalkenyl and aryl.

2. A process for providing a composition with a fragrance comprising incorporating therein an odoriferous amount of a compound selected from the group consisting of 2-(1-methoxyhexyl)furan, 2-(1-ethoxyhexyl)furan, 2-(1-methoxy-3-pentenyl)furan, 2-(1-ethoxy-4-methyl-pentyl)furan, 2-(methoxy-phenylmethyl)furan, 2-(1-methoxy-4-methylpentyl)furan and 2-(1-pentoxyethyl)furan.

* * * * *